United States Patent
Mizuno et al.

(10) Patent No.: US 9,606,249 B2
(45) Date of Patent: Mar. 28, 2017

(54) ANALYZING APPARATUS AND CALIBRATION METHOD

(71) Applicant: HORIBA, Ltd., Kyoto-shi, Kyoto (JP)

(72) Inventors: Yusuke Mizuno, Kyoto (JP); Tomoki Aoyama, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 14/712,841

(22) Filed: May 14, 2015

(65) Prior Publication Data

US 2015/0338534 A1  Nov. 26, 2015

(30) Foreign Application Priority Data

May 20, 2014  (JP) ................. 2014-104787

(51) Int. Cl.
- *G01T 7/00* (2006.01)
- *G01N 23/223* (2006.01)
- *G01N 1/22* (2006.01)
- *G01N 15/06* (2006.01)

(52) U.S. Cl.
CPC ........... *G01T 7/005* (2013.01); *G01N 1/2205* (2013.01); *G01N 15/0612* (2013.01); *G01N 23/223* (2013.01)

(58) Field of Classification Search
CPC .. G01T 7/005; G01N 1/2205; G01N 15/0612; G01N 23/223
USPC ..................................................... 378/44–48
See application file for complete search history.

(56) References Cited

U.S. PATENT DOCUMENTS

| | | | |
|---|---|---|---|
| 7,254,212 B2* | 8/2007 | Saitoh ............... | B01D 46/0002 250/308 |
| 2005/0041774 A1* | 2/2005 | Saitoh ............... | B01D 46/0002 378/53 |
| 2011/0103547 A1* | 5/2011 | Ohzawa ............. | G01N 23/223 378/45 |

FOREIGN PATENT DOCUMENTS

JP    2008261712 A    10/2008

* cited by examiner

*Primary Examiner* — Michael Maskell
(74) *Attorney, Agent, or Firm* — Brooks Kushman P.C.

(57) ABSTRACT

Calibration of an analyzing apparatus is performed using appropriate calibration data that reflects actual measurement conditions. The analyzing apparatus includes an emission unit, a collection filter, a calibration base material, a detection unit, and a composition analysis unit. The emission unit emits an exciting X-ray to generate a fluorescent X-ray by exciting particulate matter. The collection filter collects the particulate matter. The calibration base material is provided in a measurement area together with the collection filter when performing the calibration. The detection unit detects X-rays generated from the measurement area. The detection unit detects a calibration X-ray when performing the calibration. The composition analysis unit generates calibration data by using the calibration X-ray when performing the calibration. The composition analysis unit analyzes compositions of the particulate matter based on the calibration data and a measured X-ray detected by the detection unit when analyzing the compositions of the particulate matter.

4 Claims, 8 Drawing Sheets

When performing span calibration

When performing background calibration

ANALYZING APPARATUS AND CALIBRATION METHOD

CROSS-REFERENCE TO RELATED APPLICATIONS

This application claims priority to Japanese Patent Application No. 2014-104787 filed on May 20, 2014, the disclosure of which is hereby incorporated in its entirety by reference herein.

TECHNICAL FIELD

The present disclosure relates to an analyzing apparatus for analyzing particulate matter and a calibration method for calibrating the analyzing apparatus.

BACKGROUND

Recently, an apparatus for analyzing a concentration of PM 2.5 in the atmosphere and elements included in PM 2.5 has been developed in order to monitor a status of PM 2.5. It is considered that the source of PM 2.5 can be predicted by analyzing elements included in PM 2.5.

For example, JP 2008-261712A discloses a measurement apparatus for automatically and continuously analyzing kinds of elements that form floating particulate matter in the atmosphere. This measurement apparatus analyzes elements included in floating particulate matter by using fluorescence X-ray analysis of elements using an X-ray analyzer.

In the above-described measurement apparatus, an exciting X-ray is emitted to particulate matter collected on a filter. Therefore, the fluorescent X-ray generated from the particulate matter is influenced by the filter. In addition, when calibrating the measurement apparatus, calibration data is obtained in the state where the filter is removed from the measurement apparatus. However, if the calibration data without the above-described influences of the filter is used to calibrate the measurement apparatus in which the analysis of elements is performed by using the fluorescent X-ray generated from the particulate matter collected on the filter, the measurement apparatus cannot be calibrated accurately.

SUMMARY

The present disclosure provides a system and method for calibrating an analyzing apparatus for analyzing compositions using a fluorescent X-ray by using appropriate calibration data that reflect actual measurement conditions.

A plurality of embodiments for solving the problem will be described below. Aspects of these embodiments can be combined arbitrarily if required. An analyzing apparatus according to one aspect of the present disclosure is an apparatus for analyzing compositions of particulate matter based on a fluorescent X-ray generated from the particulate matter. The analyzing apparatus includes an emission unit, a collection filter, a calibration base material, a detection unit, and a composition analysis unit. The emission unit is configured to emit an exciting X-ray. The exciting X-ray excites the particulate matter to generate the fluorescent X-ray. The collection filter is configured to collect the particulate matter. The calibration base material is provided together with the collection filter in a measurement area to which the exciting X-ray is emitted when executing a calibration. The detection unit is configured to detect an X-ray generated from the measurement area. The detection unit detects a calibration X-ray generated by emitting the exciting X-ray to the collection filter and the calibration base material when performing the calibration. The composition analysis unit is configured to generate calibration data by using the calibration X-ray when performing the calibration. The composition analysis unit is configured to analyze the compositions of the particulate matter based on the calibration data and a measured value of X-rays detected by the detection unit when analyzing the compositions of the particulate matter. Thus, the analyzing apparatus can be calibrated by using the appropriate calibration data that reflects the actual measurement conditions.

It is acceptable that the collection filter has a collection layer collecting the particulate matter and a reinforcement layer reinforcing the collection layer. Thus, the collection filter can be reinforced even if the thickness of the collection film is reduced and the intensity of X-ray, which is required to calibrate the apparatus accurately, can be obtained.

It is acceptable that the calibration base material has a base material and a calibration specimen supported on the base material. It is acceptable that the composition analysis unit generates span calibration data for each element to be measured by using a base fluorescent X-ray as the calibration X-ray. The base fluorescent X-ray is generated by emitting the exciting X-ray to the calibration specimen. Thus, the span calibration can be appropriately performed for each element to be measured by using the appropriate span calibration data that reflects the influences of the collection filter.

A calibration method according to another aspect of the present disclosure is a calibration method of an analyzing apparatus for analyzing compositions of particulate matter based on a fluorescent X-ray generated from the particulate matter collected by a collection filter by emitting an exciting X-ray to the particulate matter. The calibration method includes providing a calibration base material together with the collection filter, emitting an exciting X-ray to a measurement area in which both the collection filter and the calibration base material are provided, detecting a calibration X-ray generated in response to the exciting X-ray directed to the collection filter and the calibration base material, and generating calibration data from the calibration X-ray. Thus, the analyzing apparatus can be calibrated by using the appropriate calibration data.

According to the above-described analyzing apparatus and the calibration method, the analyzing apparatus for analyzing the compositions using the fluorescent X-ray can be calibrated by using the appropriate calibration data that reflects the actual measurement conditions.

DETAILED DESCRIPTION

Figure 1:
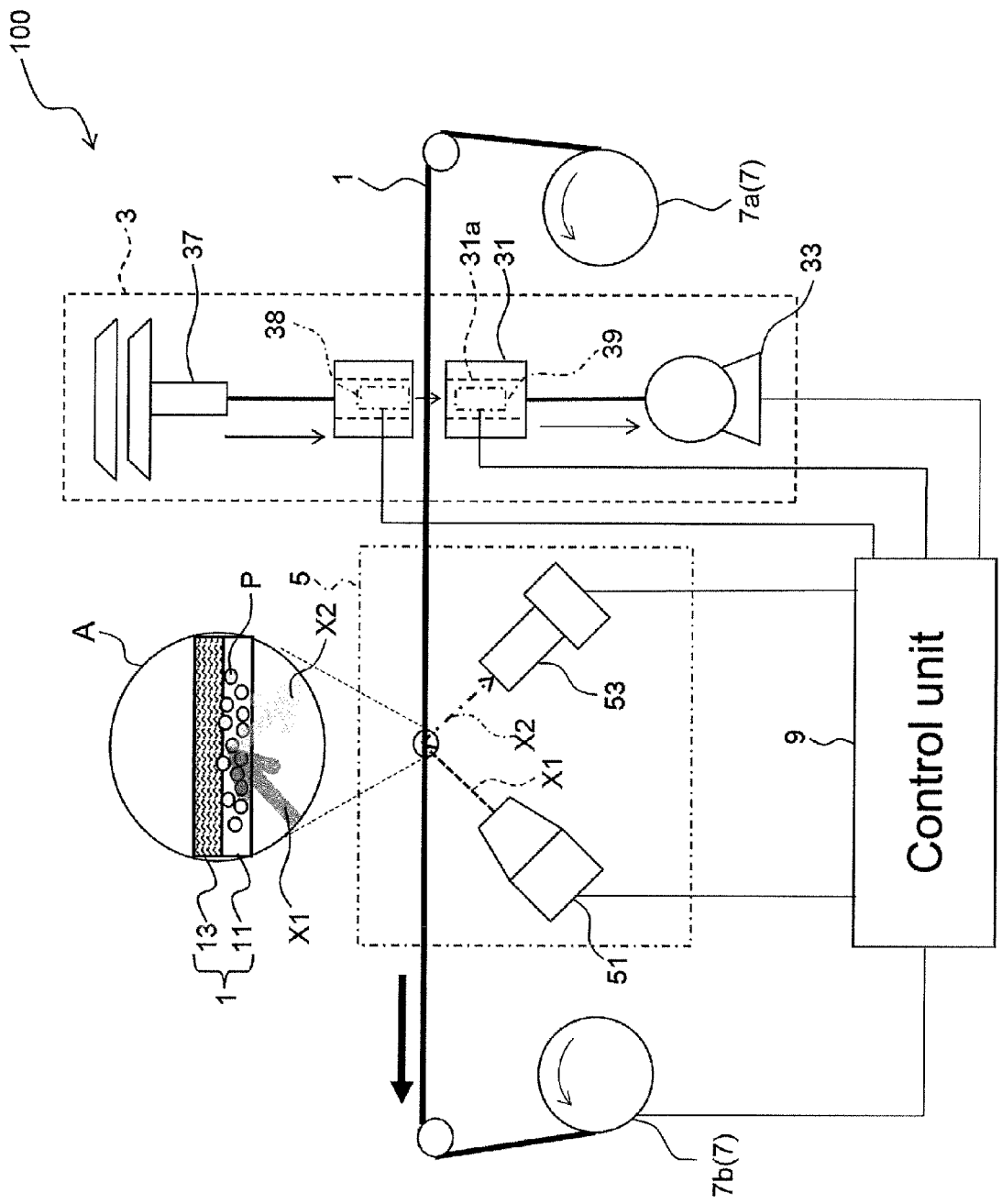
FIG. 1 shows a structure of an analyzing apparatus.

As required, detailed embodiments are disclosed herein; however, it is to be understood that the disclosed embodiments are merely illustrative and may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the teachings of the present disclosure.

First Embodiment (1) Overall Structure of an Analyzing Apparatus

An analyzing apparatus 100 according to a first embodiment will be described, referring to FIG. 1, which shows a structure of the analyzing apparatus. The analyzing apparatus 100 is the analyzing apparatus that analyzes compositions of particulate matter P (described later) based on a florescent X-ray generated from the particulate matter P by emitting an exciting X-ray X1 (described later) to the particulate matter P. The analyzing apparatus 100 includes a collection filter 1, a sampling unit 3, analysis unit 5, a filter moving unit 7, and a control unit 9.

The collection filter 1 collects the particulate matter P included in the sampled atmosphere. The collection filter 1 has a collection layer 11 that has pores for trapping the particulate matter P. Fluorine-based resin (for example, polytetrafluoroethylene (PTFE)) can be used as the material of the collection layer 11, for example.

The thickness of the collection layer 11 is adjusted such that the absorption of an X-ray, such as the exciting X-ray and the fluorescent X-ray, is less than a predetermined level. In the present embodiment, the thickness of the collection layer 11 is 3 to 35 μm.

As shown in FIG. 1, the collection filter 1 has a reinforcement layer 13 on the main surface of the collection layer 11 to reinforce the collection layer 11. Thus, the collection filter 1 can be strong enough to endure the suction power of the sampling unit 3 during sampling the atmosphere including the particulate matter P using the sampling unit 3.

Materials that pass a gas, include no or little of the element to be measured, and have sufficient strength are chosen for the reinforcement layer 13. Non-woven fabrics of polyethylene, polypropylene, polyethylene terephthalate (PET), nylon, polyester, and/or polyamide can be used as the material for the reinforcement layer 13. Especially, the non-woven fabric of polypropylene and polyester enables accurate measurement because such non-woven fabric has sufficient strength and does not include impurities that can be noise for the fluorescent X-ray analysis.

In addition, since a non-woven fabric is a fabric in which fibers are bonded with each other with sufficient bonding strength, it is porous and has abundant cavities. Therefore, by using a non-woven fabric as the reinforcement layer 13, the tensile strength of the collection filter 1 can be increased even if the thickness is small. Consequently, the thickness of the collection filter 1 can be adjusted such that the absorption of X-rays is less than the predetermined level.

The overall thickness of the collection filter 1 that has the collection layer 11 and the reinforcement layer 13 is between 100 and 200 μm in average. In the present embodiment, the thickness of the collection filter 1 is 140 μm on average.

The sampling unit 3 samples the atmosphere around the analyzing apparatus 100 and sprays the sampled atmosphere onto the collection filter 1. For example, in the sampling unit 3, the atmosphere, which is suctioned from a sampling port 37 by the suction pump 33, is sprayed onto the collection filter 1 by the suction power of the suction pump 33. It should be noted that a meshed support member that supports the collection filter 1 may be arranged in a first opening 31a (FIG. 1).

The sampling unit 3 includes a β-ray emission unit 38 and a β-ray detection unit 39. A particle mass concentration calculation unit 96 (FIG. 2) of a control unit 9 measures a particle mass concentration of the particulate matter P collected by the collection filter 1, based on an intensity of a β-ray that is emitted by the β-ray emission unit 38, passes through the collection filter 1 and the particulate matter P, and is detected by the β-ray detection unit 39.

The analysis unit 5 analyzes elements (compositions) that are included in the particulate matter P. In the present embodiment, the analysis unit 5 analyzes mainly metallic elements that are included in the particulate matter P. Metallic elements included in the particulate matter P may include sodium, aluminum, calcium, titanium, vanadium, manganese, zinc, lead, barium, antimony, lanthanum, and samarium. In addition, the analysis unit 5 also analyzes elements other than metallic elements such as sulfur, chlorine, bromine, etc.

The filter moving unit 7 moves the collection filter 1 such that the collection filter 1 is moved by forwarding the collection filter 1 from a forwarding reel 7a while winding the collection filter 1 to a winding reel 7b of the filter moving unit 7. The control unit 9 controls the analyzing apparatus 100. The control unit 9 also inputs the X-ray data detected by the detection unit 53 of the analysis unit 5 and performs various operations using the inputted X-ray data.

(2) Structure of an Analysis Unit

Next, the structure of the analysis unit 5 will be described. The analysis unit 5 generates the fluorescent X-ray from the particulate matter P collected by the collection filter 1 to detect it. Therefore, the analysis unit 5 includes an emission unit 51 and a detection unit 53. The emission unit 51 emits the exciting X-ray X1 to the measurement area A. The particulate matter P sampled by the sampling unit 3 is sent to the measurement area A when the analyzing apparatus 100 analyzes elements included in the particulate matter P.

In the present embodiment, the emission unit 51 is an X-ray generator that outputs (emits) the exciting X-ray X1. A primary filter (not shown in the figure) is provided at the exit of the emission unit 51 through which the exciting X-ray exits. The primary filter reduces the intensity of the exciting X-ray in the wavelength ranges that correspond to the wavelengths of the fluorescent X-ray generated from elements to be measured. Thus, the background component of the X-ray detected by the detection unit 53 can be reduced.

The detection unit 53 detects the X-ray X2 generated from the measurement area A by emitting the above-described exciting X-ray X1 to the measurement area A. For example, a semiconductor detector, such as a silicon semiconductor detector, a silicon drift detector (SDD), etc., can be used as the detection unit 53. When using a semiconductor detector as the detection unit 53, the detection unit 53 outputs pulse signals having the predetermined maximum voltage or the predetermined maximum current (a maximum signal value) when an X-ray X2 enters the detection unit 53.

(3) Structure of Control Unit

Figure 2:
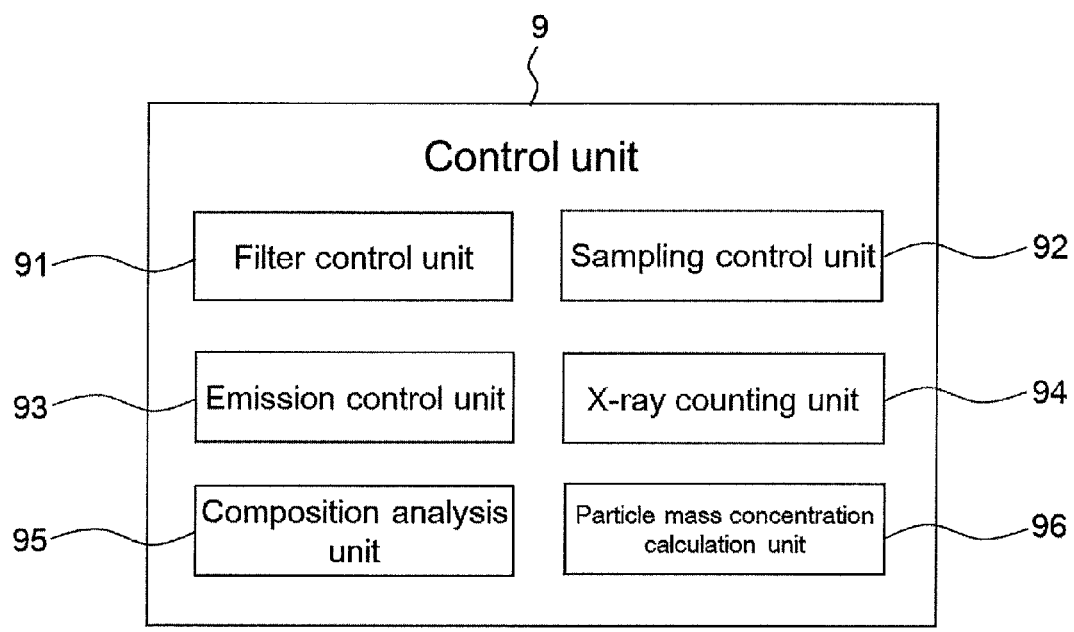
FIG. 2 shows a structure of a control unit.

Next, the structure of the control unit 9 will be described, referring to FIG. 2. which shows the structure of the control unit. The control unit 9 is a computer system that has a central processing unit (CPU), a storage apparatus such as a read only memory (ROM), a hard drive, etc., a display, and interfaces. The functions of some or all of the elements of the control unit 9 described below may be realized by a program stored in the storage apparatus of the above computer system. In addition the functions of some or all of the elements of the control unit 9 may be realized by a semiconductor device such as a customized IC.

The control unit 9 includes a filter control unit 91, a sampling control unit 92, an emission control unit 93, an X-ray counting unit 94, a composition analysis unit 95, and the above-described particle mass concentration calculation unit 96. The filter control unit 91, for example, controls the rotation of a motor (not shown in the figure) that controls the rotation of the winding reel 7b. In addition, the filter control unit 91 controls the pushing force of the collection filter 1.

The sampling control unit 92 controls the sampling unit 3, for example, by controlling the suction power of the suction unit 31 and the flow rate of the atmosphere in the sampling unit 3.

The emission control unit 93 adjusts the intensity of the exciting X-ray X1. The X-ray counting unit 94 counts the number of the pulse signals from the detection unit 53 within the predetermined signal value range and outputs the counting result. The composition analysis unit 95 calibrates the analysis unit 5 and analyzes compositions (elements) of the particulate matter P.

(4) Operation of Analyzing Apparatus

I. Calibration Method

First, the calibration of the analyzing apparatus 100 (the analysis unit 5) will be described. In the composition analysis performed by the above-described analyzing apparatus 100, measurement area A includes various X-rays generated due to the existence of the collection filter 1, in addition to the fluorescent X-ray generated from the particulate matter P. Specifically, the X-ray X2 includes the fluorescent X-ray generated by emitting the exciting X-ray X1 to the collection filter 1, and the scattered X-ray generated when the exciting X-ray X1 is scattered by the collection filter 1.

In addition, the exciting X-ray X1 is absorbed by the collection filter 1 until the exciting X-ray X1 reaches the particulate matter P. Some fluorescent X-rays generated from the particulate matter P are absorbed by the collection filter 1 until it reaches the detection unit 53.

Figure 3:
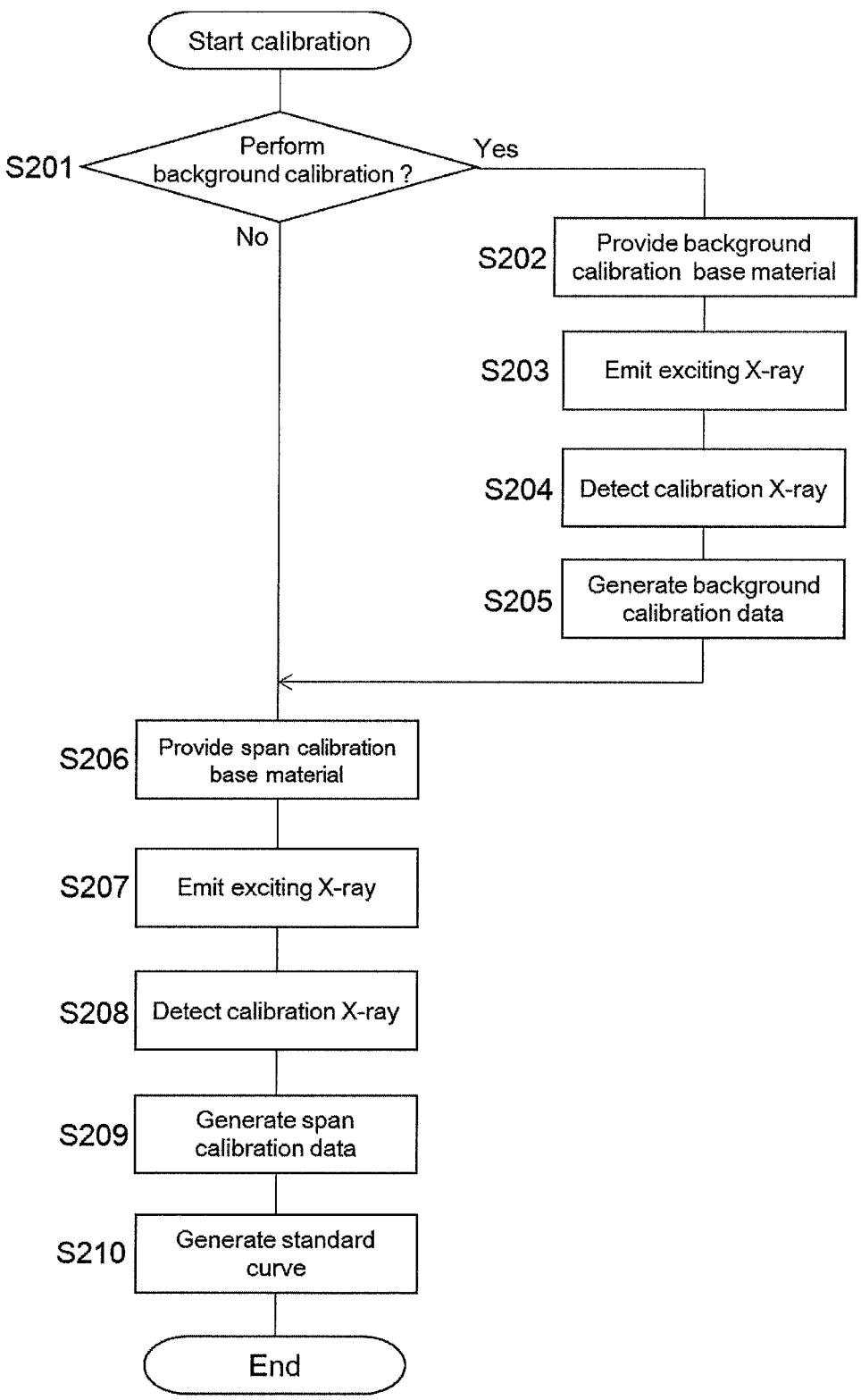
FIG. 3 is a flowchart that shows a calibration method.

Therefore, in the present embodiment, the calibration of the analysis unit 5 that reflects the above influences caused by the existence of the collection filter 1 is performed by way of the calibration method described below using FIG. 3, which shows a flowchart of the calibration method.

First, the composition analysis unit 95 determines whether a background calibration should be performed or not (step S201). For example, if no background data is stored in the storage apparatus of the control unit 9, etc., the background calibration is performed. If the composition analysis unit 95 determines that the background calibration is performed (if "Yes" in step S201), the process proceeds to step S202 to generate the background data (i.e., performing the background calibration). On the other hand, if the composition analysis unit 95 determines that the background calibration is not performed (if "No" in step S201), the process proceeds to step S206 to generate span calibration data (i.e., performing a span calibration).

When performing the background calibration, the collection filter 1 is first moved such that a no-collection area of the collection filter 1, on which no or little particlulate matter P is collected, exists in the measurement area A.

Figure 4B:
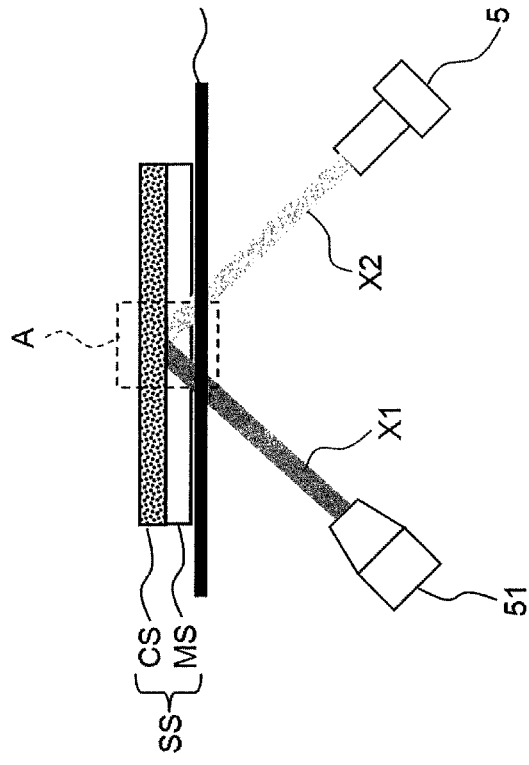
FIG. 4B shows a state in which a calibration base material is provided on a main surface of a collection filter when performing span calibration.
Figure 4A:
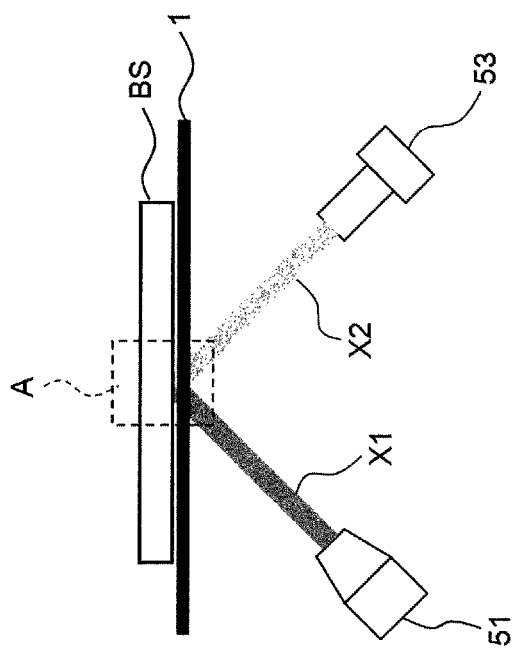
FIG. 4A shows a state in which a calibration base material is provided on a main surface of a collection filter when performing background calibration.

Next, a background calibration base material BS is provided as the calibration base material, by the user or automatically, on the main surface of the collection filter 1 and in the measurement area A as shown in FIG. 4A (step S202), together with the collection filter. FIG. 4A shows the state in which the calibration base material is provided on the main surface of the collection filter. The background calibration base material BS is the base material, such as polycarbonate base material, which is made of a material substantially "transparent" to the exciting X-ray X1 and the fluorescent X-ray X2 (the material that passes the X-rays).

After providing the background calibration base material BS, the exciting X-ray X1 is emitted to the measurement area A (step S203). While the exciting X-ray X1 is emitted, the detection unit 53 detects the X-ray X2 as a calibration X-ray that is generated by emitting the exciting X-ray X1 to the collection filter 1 and/or the background calibration base material BS (step S204).

Figure 5:
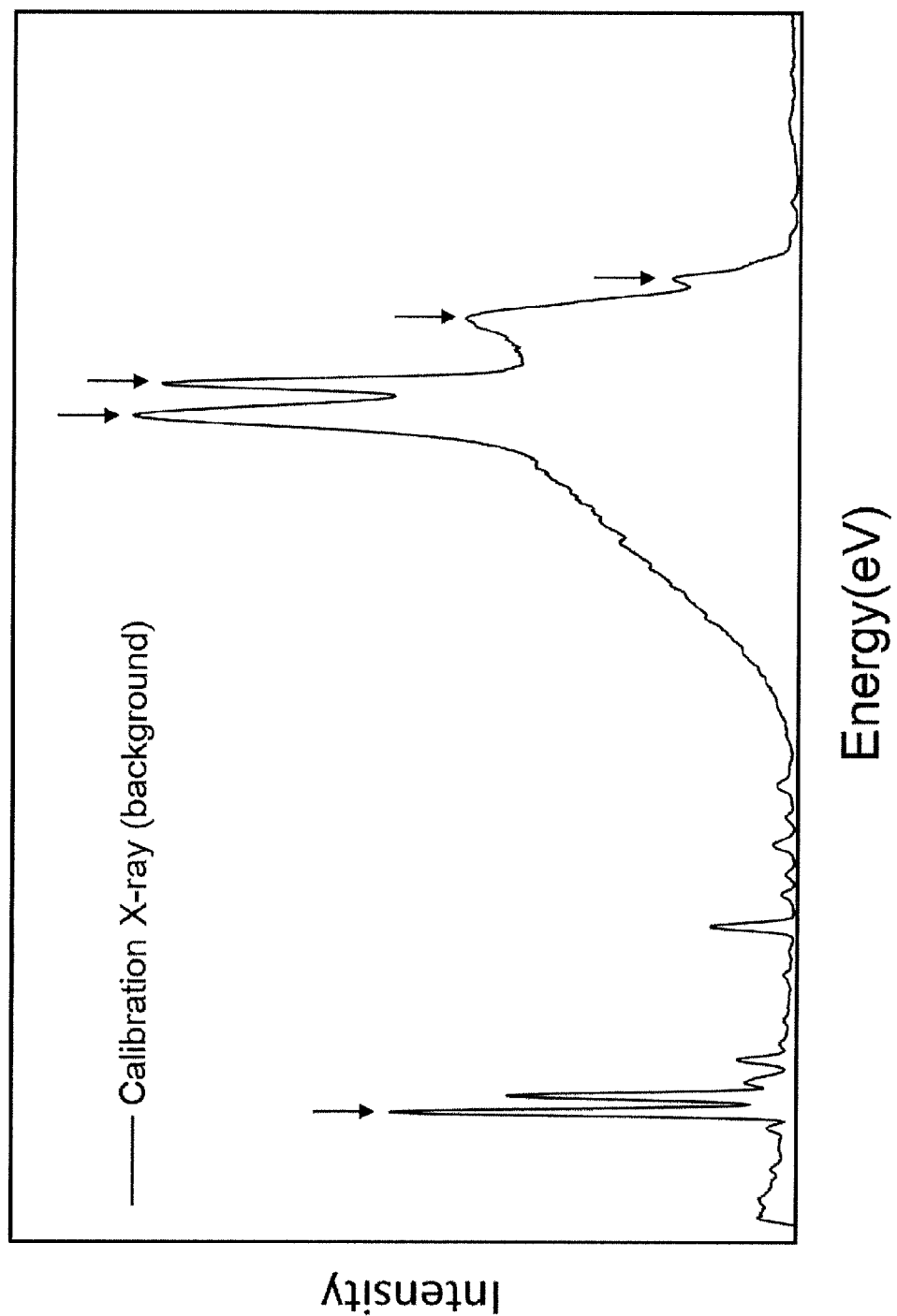
FIG. 5 shows one example of a profile of a calibration X-ray.

If the counting results of the above-described calibration X-ray are plotted on the graph in which the horizontal axis is the energy of X-ray and the vertical axis is the intensity of X-ray, the profile as shown in FIG. 5, for example, can be obtained. FIG. 5 shows one example of the profile of the calibration X-ray. The arrows in FIG. 5 show the energy peaks included in the exciting X-ray X1.

After counting the calibration X-ray, the composition analysis unit 95 generates the background calibration data by associating the counting results of the calibration X-ray at the energy values of the fluorescent X-ray of each of elements to be measured (the elements to be analyzed by the analyzing apparatus 100) with these energy values, and stores the generated background calibration data (step S205). Alternatively, the composition analysis unit 95 may generate the numerical data as the background calibration data that generates the profile of the calibration X-ray as shown in FIG. 5 (the numerical data that includes the group of a plurality of energy values and the group of the numbers of the pulse signals at the corresponding energy values). Thus, the background values in the whole energy range detectable with the detection unit 53 can be stored.

After generating the background calibration data, or if the composition analysis unit 95 determines that the background calibration is not performed, the composition analysis unit 95 performs the span calibration. When the span calibration starts, a span calibration base material SS is provided, by the user or automatically, in the measurement area A together with the collection filter 1 (step S206). It is preferable that the no-collection area of the collection filter 1 is entered in the measurement area A also when performing the span calibration. Otherwise, the span calibration data may be in error if the particulate matter P remains in the collection filter 1 due to the florescent X-ray generated from the particulate matter P remaining in the measurement area A.

The span calibration base material SS has a base material MS and a calibration specimen CS, as shown in FIG. 4B. The base material MS is the substrate made of the same material (polycarbonate, for example) as that of the background calibration base material BS. The calibration specimen CS is the material in which at least elements included in the particulate matter P (the elements to be measured) are included. The predetermined amount of the calibration specimen CS is supported on the base material MS. The standard material, which is officially approved by National Institute of Standards & Technology (NIST), can be used as the calibration specimen CS, for example. Thus, the accurate composition analysis can be performed by using the standard material that is broadly approved in the world.

In addition, the calibration specimen CS is preferably the particulate matter similar to the particulate matter P to be measured. This is because the fluorescent X-ray generated by emitting the exciting X-ray X1 to the particulate matter P is influenced by the particle state (the amount of water included in the particulate matter and the diameters of the particles) of the particulate matter P.

After providing the span calibration base material SS, the exciting X-ray X1 is emitted to the measurement area A (step S207) and then the fluorescent X-ray (a base fluorescent X-ray) is generated from the elements included in the calibration specimen CS.

Figure 6:
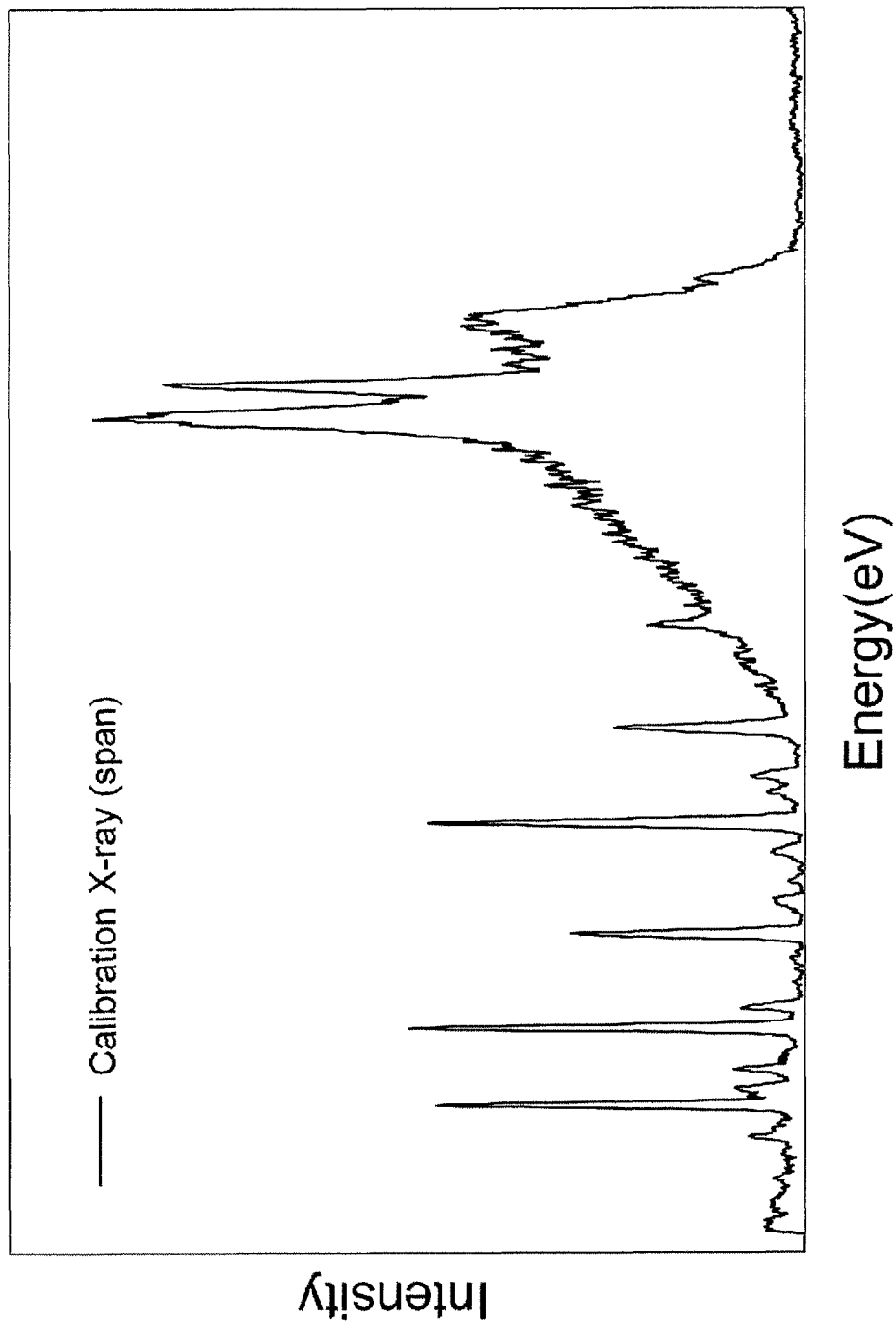
FIG. 6 shows one example of a calibration X-ray including a base fluorescent X-ray.

The detection unit 53 detects the X-ray X2 generated by emitting the exciting X-ray X1 to the measurement area as the calibration X-ray (step S208). If the counting results of this calibration X-ray are plotted on the graph in which the horizontal axis is the energy value of X-ray and the vertical axis is the intensity of X-ray, the profile shown in FIG. 6 can be obtained, for example. FIG. 6 shows one example of the calibration X-ray including the base fluorescent X-ray. The calibration X-ray, obtained as described above, mainly includes the scattered X-ray generated when the exciting X-ray X1 is scattered by the collection filter 1, and a base fluorescent X-ray generated from the calibration specimen CS.

After counting the calibration X-ray, the composition analysis unit 95 generates the span calibration data by associating the intensities (the numbers of the pulse signals) of the calibration X-ray (obtained in step S208) at the energy values that are inherent for each of the fluorescent X-rays generated from each of the elements to be measured, with the intrinsic energy values and the amounts of the elements that generates the fluorescent X-rays having the intrinsic energy values (step S209). The amounts of the elements can be derived from the amount of the calibration specimen CS supported on the base material MS.

Alternatively, the composition analysis unit 95 may use, as the span calibration data, the numerical data that is obtained by subtracting the numerical data that generates the profile of the calibration X-ray of the background calibration as shown in FIG. 5, from the numerical data that generates the profile of the calibration X-ray including the base fluorescent X-ray as shown in FIG. 6.

By generating the span calibration data using the above-described calibration X-rays, the appropriate span calibration data that reflects the actual measurement conditions in which the influences of the collection filter 1 are taken into consideration, can be generated. After generating the background calibration data and the span calibration data, the composition analysis unit 95 generates standard curves, which show the relationship between the intensity of the fluorescent X-ray and the amount of the element to be measured, for each of the elements to be measured (step S210).

Figure 7:
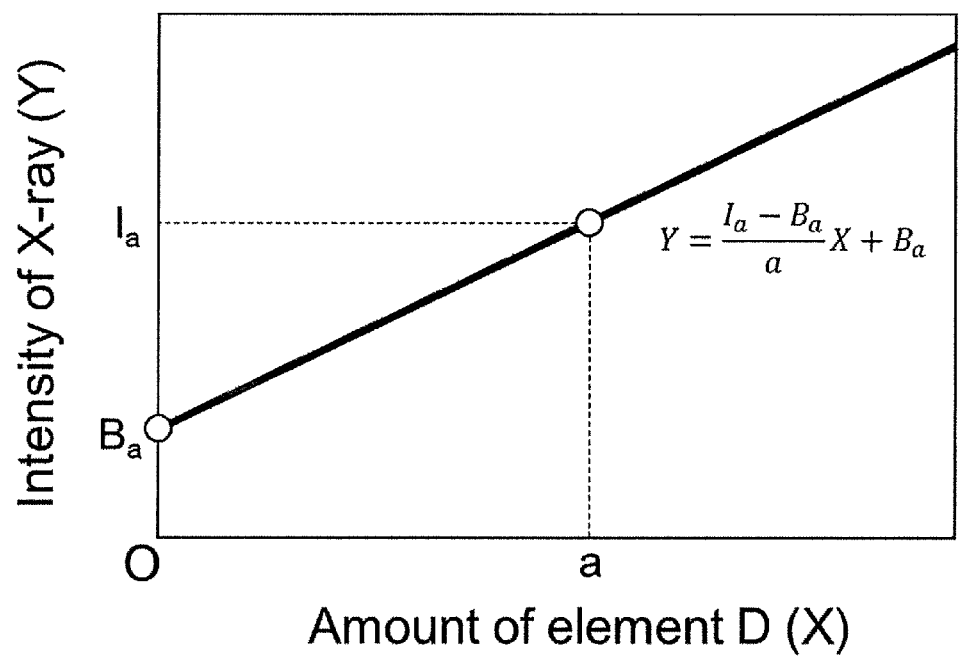
FIG. 7 shows one example of a standard curve for an element D.

Specifically, when the standard curve for element D to be measured is generated for example, the standard curve for element D is generated as the formula that expresses, as shown in FIG. 7, the straight line with the intercept $B_a$ and the slope $(I_a-B_a)/a$ plotted on the graph in which the horizontal axis is the amount of the element D and the vertical axis is the intensity of X-ray, where $B_a$ is the intensity of X-ray of the background calibration data at the energy value of the fluorescent X-ray generated from the element D, $I_a$ is the intensity of X-ray of the span calibration data at the energy value of the fluorescent X-ray generated from the element D, and "a" in the above formula is the amount of the element D existed in the measurement area A during obtaining the span calibration data. FIG. 7 shows one example of the standard curve for the element D. In other words, assuming that X is the amount of the element D and Y is the intensity of the detected X-ray, the composition analysis unit 95 generates the formula $Y=((I_a-B_a)/a)*X+B_a$ as the standard curve for the element D.

By generating the standard curve using the above-described calibration data, the appropriate (more accurate) standard curve that reflects the actual measurement conditions can be generated. In other words, the calibration of the analysis unit 5 in which the influences of the collection filter 1 are taken into consideration can be appropriately performed. It should be noted that, if the energy value of the peak of the fluorescent X-ray, obtained when performing the span calibration using the span calibration base material SS, is shifted from the energy value at which the peak should appear, the detection unit 53 is adjusted such that the peak of the fluorescent X-ray appears at the proper energy value.

II. Method of Analyzing Compositions of Particulate Matter

Next, the method of analyzing compositions (elements) of the particulate matter P will be briefly described. First, the particulate matter P included in the atmosphere is collected to the collection filter 1 by the sampling unit 3, then the collected particulate matter P is moved into the measurement area A by the filter moving unit 7.

Figure 8:
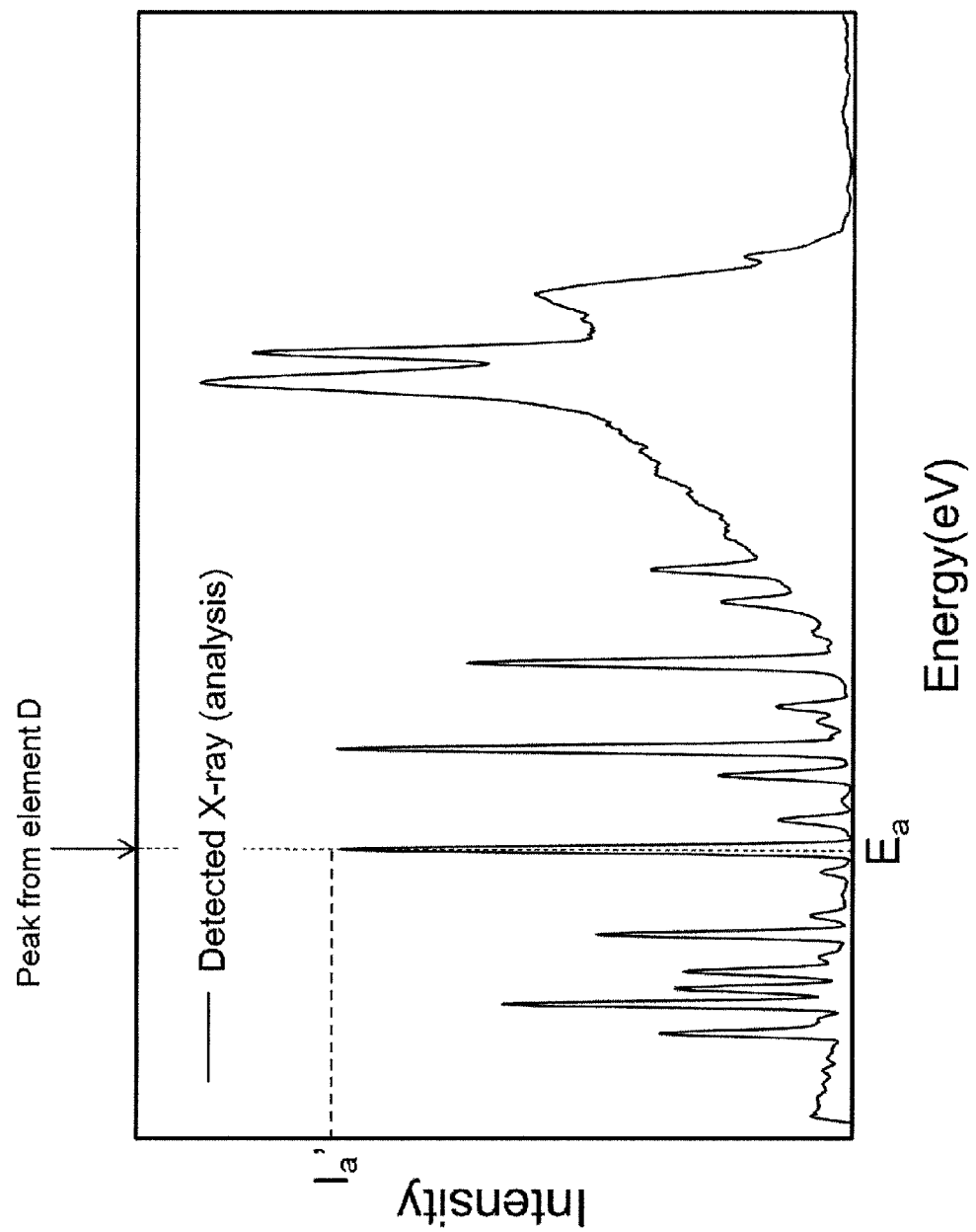
FIG. 8 shows one example of a profile of an X-ray including a fluorescent X-ray from particulate matter.

Next, the composition analysis unit 95 quantifies the amounts of elements included in the particulate matter P based on the above-described calibration data (the standard curve) and the measurement value of the X-ray X2 detected by the detection unit 53, which is generated from the measurement area A in which the collected particulate matter P exists by emitting the exciting X-ray X1. For example, assume that the amount of the element D (assume that the energy value of the fluorescent X-ray generated from the element D is $E_a$) is quantified when the profile that shows the relationship between the energy value of X-ray and the intensity of X-ray, as shown in FIG. 8, is obtained. FIG. 8 shows one example of the profile of the X-ray including the fluorescent X-ray from the particulate matter.

The composition analysis unit 95 first substitutes $I_a'$ for Y in the equation $Y=((I_a-B_a)/a)*X+B_a$ that expresses the standard curve for the element D. Then, the composition analysis unit 95 can accurately quantify the amount of the element D collected by the collection filter 1 as $((Ia'-Ba)/(Ia-Ba))*a$ by solving the above equation $I_a'=((I_a-B_a)/a)*X+B_a$ for X.

Other Embodiments

One embodiment of the present disclosure has been described above. However, the present disclosure is not limited to the above-described embodiment and various modifications can be made in the scope of the present disclosure.

(A) Other Embodiment of Span Calibration

A plurality of span calibration data sets may be generated by using a plurality of the span calibration base materials SS with various supporting amounts of the calibration specimen CS and then the standard curve may be generated by using the plurality of the span calibration data. Thus, the standard curve can be accurately generated even if the intensity of the fluorescent X-ray is not linearly increased as the amount of the element increases, for example. Alternatively, the standard curve may be calibrated by multiplying the standard curve before the calibration by the ratio of the present span calibration data to the previous span calibration data.

(B) Other Embodiment of Calibration Method

In the above-described analyzing apparatus 100 according to the above-described first embodiment, the span calibration (performed approximately once a month) and the background calibration, which is performed less frequently than the span calibration, are performed as the calibrations for the analysis unit 5. However, the calibrations are not limited to these and various other calibrations may also be performed.

For example, the intensities of X-rays that depend on each of the elements to be measured may be calibrated by first measuring the intensities of the scattered X-ray at both a standard timing and the timing when the composition analysis starts, then calculating the ratio of the intensity of the scattered X-ray measured at the standard timing and the intensity of the scattered X-ray measured at the timing when the composition analysis starts. In addition, the influences caused by the changes of the particulate matter P due to the changes of the environment (temperature, humidity, and atmospheric pressure) around the analyzing apparatus 100 may be calibrated. Moreover, for example, the peak shifts in the counting result may be calibrated in the simple way that uses the peaks included in the scattered X-ray and having the known and unchanged energy values.

The claimed subject matter of the present disclosure can be widely applied to the analyzing apparatus for analyzing particulate matter.

While illustrative embodiments are described above, it is not intended that these embodiments represent all possible forms of the claimed subject matter. The words used in the specification are words of description rather than limitation, and it is understood that various changes may be made without departing from the spirit and scope of the disclosure. Additionally, the features of various implementing embodiments may be combined to form further embodiments of the disclosure that may not be explicitly illustrated or described.

What is claimed is:

1. An analyzing apparatus for analyzing compositions of particulate matter based on a fluorescent X-ray generated from the particulate matter, the analyzing apparatus comprising:
    an emission unit configured to emit an exciting X-ray, the exciting X-ray exciting the particulate matter to generate the fluorescent X-ray;
    a collection filter configured to collect the particulate matter;
    a calibration base material provided together with the collection filter in a measurement area to which the exciting X-ray is emitted when performing a calibration;
    a detection unit configured to detect an X-ray generated from the measurement area, the detection unit detecting a calibration X-ray generated from the measurement area by emitting the exciting X-ray to the collection filter and the calibration base material when performing the calibration,
    the calibration base material having a base material and a calibration specimen supported on the base material; and
    a composition analysis unit configured to generate span calibration data for each element to be measured by using a base fluorescent X-ray as the calibration X-ray when performing the calibration, the base fluorescent X-ray being generated by emitting the exciting X-ray to the calibration specimen,
    and analyze the compositions of the particulate matter based on the span calibration data and a measured value of X-ray detected by the detection unit when analyzing the compositions of the particulate matter.

2. The analyzing apparatus according to claim 1, wherein the collection filter has a collection layer collecting the particulate matter and a reinforcement layer reinforcing the collection layer.

3. A calibration method of an analyzing apparatus for analyzing compositions of particulate matter based on a fluorescent X-ray generated from the particulate matter collected by a collection filter by emitting an exciting X-ray to the particulate matter, the calibration method comprising:
    providing a calibration base material together with the collection filter, the calibration base material having a base material and a calibration specimen supported on the base material;
    emitting the exciting X-ray to a measurement area in which both the collection filter and the calibration base material are provided;
    detecting a calibration X-ray, the calibration X-ray being generated by emitting the exciting X-ray to the collection filter and the calibration base material; and
    generating span calibration data for each element to be measured by using a base fluorescent X-ray as the calibration X-ray,
    the base fluorescent X-ray being generated by emitting the exciting X-ray to the calibration specimen.

4. The analyzing apparatus of claim 1, wherein the composition analysis unit is further configured to generate background calibration data using an X-ray generated by emitting the exciting X-ray to the base material as the calibration X-ray, and analyze the composition of the particulate matter based on the background calibration data and the measured value of X-ray detected by the detection unit when analyzing the composition of the particulate matter.

* * * * *